United States Patent [19]

Hinze et al.

[11] Patent Number: 4,576,947

[45] Date of Patent: Mar. 18, 1986

[54] PHARMACEUTICAL COMPOSITIONS

[75] Inventors: Heinz-Joachim Hinze, Auringen; Alfons Söder, Frankfurt-Schwanheim; Kurt Popendiker, Wiesbaden, all of Fed. Rep. of Germany

[73] Assignee: Hoechst Aktiengesellschaft, Frankfurt, Fed. Rep. of Germany

[21] Appl. No.: 543,114

[22] Filed: Nov. 10, 1983

Related U.S. Application Data

[63] Continuation of Ser. No. 774,648, Mar. 4, 1977, abandoned, which is a continuation-in-part of Ser. No. 485,870, Jul. 5, 1974, abandoned, which is a continuation-in-part of Ser. No. 330,653, Feb. 8, 1973, abandoned.

[30] Foreign Application Priority Data

Feb. 15, 1972 [DE] Fed. Rep. of Germany ....... 1810705
Feb. 19, 1972 [DE] Fed. Rep. of Germany ....... 2207860
Jul. 11, 1973 [DE] Fed. Rep. of Germany ....... 2335170

[51] Int. Cl.⁴ .................................... A61K 31/52
[52] U.S. Cl. ........................... 514/263; 544/267
[58] Field of Search .............. 514/263; 544/267; 424/253

[56] References Cited

U.S. PATENT DOCUMENTS 2,953,493  9/1960  Schroeder et al. .............. 424/253
3,632,742  1/1972  Eckert et al. ................... 424/253
3,864,469  2/1975  Reiser et al. ................... 424/253
4,515,795  5/1985  Hinze et al. .................... 514/263

OTHER PUBLICATIONS

Archiv. der Pharmazie, vol. 299, (1966), pp. 448–456.
Dissertationes Pharmaceuticae et Pharmacological, vol. XX, pp. 497–505, (1968).

*Primary Examiner*—John Kight
*Assistant Examiner*—M. L. Moore
*Attorney, Agent, or Firm*—Berman, Aisenberg & Platt

[57] ABSTRACT

A pharmaceutical composition containing as an essential ingredient a compound of the formula

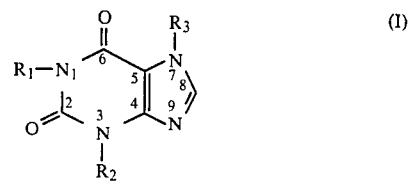

wherein one of the groups $R_1$, $R_2$ and $R_3$ is an ω- or (ω-1)-hydroxyalkyl group having from 5 to 8 carbon atoms in which the hydroxy group is separated from the xanthine nucleus by at least 2 carbon atoms, radicals $R_1$ and $R_3$ which are no hydroxylalkyl group, are hydrogen or methyl and equal or different, and $R_2$ is said hydroxyalkyl group or methyl, a compound of formula (I) and a pharmaceutical product for treatment of diseases involving insufficiency of cerebral blood flow.

20 Claims, No Drawings

PHARMACEUTICAL COMPOSITIONS

This application is a continuation of application Ser. No. 774,648, filed Mar. 4, 1977 now abandoned, which is a continuation-in-part application of U.S. application Ser. No. 485,870, filed July 5, 1974 now abandoned, which again is a continuation-in-part application of U.S. application Ser. No. 330,653, filed Feb. 8, 1973 now abandoned.

This invention relates to hydroxyalkyl-mono- or -dimethyl-xanthines and to pharmaceutical compositions containing them for use in the treatment of diseases involving insufficiency of cerebral blood flow.

7-(2-Hydroxypropyl)-1,3-dimethyl-xanthine, 7-(2,3-dihydroxypropyl)-1,3-dimethylxanthine and 1-(2-hydroxypropyl)-3,7-dimethylxanthine are compounds that may, advantageously, be used as bronchodilatory or coronary agents. These compounds possess significant pharmacological properties, in particular they may increase the rate of blood circulation. The compounds possess a greater degree of water solubility and/or lower toxicity than theobromine, theophylline and trialkylxanthines; however these advantages are only gained at the cost of reduced pharmacological activity of the compound.

We have now found that dimethylxanthines containing a longer chain (4-8, preferably 5-8 carbon atoms) hydroxyalkyl group in any of the 1-, 3- or 7-positions possess improved properties as compared to the hydroxypropyl compounds because they act to improve cerebral blood flow. Such compounds have a long and powerful action on cerebral blood flow. In possessing such properties the compounds surprisingly differ completely from the previously described or known short chain hydroxy alkyl derivatives of theophylline and theobromine. 1,3-Dimethylxanthine-ethylene-diamine also increases the cerebral blood flow, but only to a limited extent and only for a short time. Compounds, in which the hydroxyalkyl group is in the 7-position, and particularly those in which the hydroxy group is in the (ω-1)-position, also have a strong broncholytic effect. In other aspects, the pharmacological activity of the substances proposed according to the invention substantially coincides with that of known short chain hydroxyalkyl derivatives of theophylline and theobromine and their toxicity is low.

According to the invention there is provided a pharmaceutical composition containing as an essential ingredient a compound of the formula

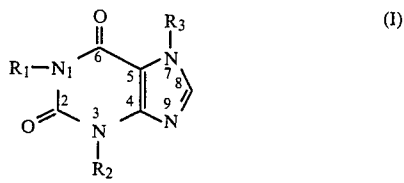

(I)

wherein

R₁ is a member selected from the group consisting of branched or unbranched ω-hydroxyalkyl having from 4 to 8, preferably from 5 to 8 carbon atoms and in which the hydroxyl is separated from the xanthine nucleus by at least two carbon atoms, unbranched (ω-1)-hydroxyalkyl having 5, 7 or 8 carbon atoms, branched (ω-1)-hydroxyalkyl having from 5 to 8 carbon atoms and in which the hydroxyl is separated from the xanthine nucleus by at least two carbon atoms, methyl and —H;

R₂ is a member selected from the group consisting of branched or unbranched ω-hydroxyalkyl having from 4 to 8, preferably from 5 to 8 carbon atoms and in which the hydroxyl is separated from the xanthine nucleus by at least two carbon atoms, unbranched (ω-1)-hydroxyalkyl having from 5 to 8 carbon atoms branched (ω-1)-hydroxyalkyl having from 4 to 8, preferably from 5 to 8 carbon atoms and in which hydroxyl is separated from the xanthine nucleus by at least two carbon atoms, and methyl; and R₃ is a member selected from the group consisting of branched or unbranched ω-hydroxyhexyl, unbranched (ω-1)-hydroxyalkyl having from 4 to 8, preferably from 5 to 8 carbon atoms, branched (ω-1)-hydroxylalkyl having from 5 to 8 carbon atoms and in which the hydroxyl is separated from the xanthine nucleus by at least two carbon atoms, methyl and —H;

one and only one of R₁, R₂ and R₃ being ω- or (ω-1)-hydroxyalkyl.

As it is evident from the compounds specifically recited herein-below and in examples 1 to 18 those hydroxyalkyl compounds are preferred in which the hydroxy group is separated from the xanthine nucleus by at least 3 carbon atoms or in other words wherein the carbon atom to which the hydroxy grooup is bound is separated from the xanthine nucleus by at least 2 carbon atoms.

Thus, according to one embodiment of the invention in the compounds of formula (I) one of the groups R₁, R₂ and R₃ is a—preferably unbranched—hydroxyalkyl group having from 5 to 8 carbon atoms in which the carbon atom to which the hydroxy group is bound is separated from the xanthine nucleus by at least 3 carbon atoms. In a further preferred embodiment radicals R₁ and R₃ which are a radical other then hydroxyalkyl group, are hydrogen or methyl and the same or different, and R₂ is said hydroxyalkyl group or methyl.

In another preferred embodiment R₂ is methyl; in a further preferred embodiment R₂ and either R₁ or R₃ is methyl. In a further preferred embodiment the hydroxyalkyl group is R₁ or R₃, and the hydroxy group is preferably in the ω- or the (ω-1)-position. From the compounds of formula (I) in which the hydroxyl group of the hydroxyalkyl group is in the (ω-1)-position, we particularly prefer to use 1-(5-hydroxyhexyl)-3,7-dimethylxanthine because of its advantageous properties in improving cerebral blood flow.

The pharmaceutical composition according to the invention may contain at least one further active ingredient and may be presented in a form suitable for oral, parenteral or rectal administration. They may thus be administered in solid form or in solution. The pharmaceutical processing to yield the conventional application forms such as solutions, emulsions, tablets, coated tablets, suppositories, granulates or sustained release forms takes place in conventional manner using conventional adjuvants, carriers or excipients, disintegrants, binders, coating agents, swelling substances, lubricants, flavouring agents, sweetening agents, agents for obtaining a sustained release effect or solubilisers.

It is also possible for the preparation to contain vitamins. Another possibility is for the preparation to contain compound (I) in combination with at least one therapeutically reactive substance in such an intimate admixture that the preparation shows a delayed release of an active substance. By the same intimate admixture it is also possible for normally unstable vitamins therein to be stabilized.

The carrier or excipient may be pharmaceutically inert or pharmaceutically active. Suitable excipients are e.g. lactose, mannitol, talc or substances having a swelling action, e.g. milk portein, starch, gelatine, cellulose or its derivatives, such as methyl cellulose and hydroxyethyl cellulose, or suitable copolymers having a swelling or non-swelling action. By means of such excipients which can be added in larger or smaller proportions the disintegration of the composition and therefore the release of the active substance can be influenced.

The compounds used in the pharmaceutical compositions according to the invention are so readily soluble in sterile water that they can be administered parenterally. Therefore it is possible to prepare a composition containing the essential ingredient in an essential non-toxic concentration which is effective for increasing cerebral blood flow of a subject to which the composition is administered.

The pharmaceutical compositions may be in the form of an injectable solution of a compound of formula (I) in sterile water obtained, for example, by twice distilling water. Alternatively the pharmaceutical compositions may be presented in a solid dosage unit form if desired with an effect of delayed release. Each dosage unit is adapted to supply a fixed quantity of active ingredient and may contain 10 to 1000 mg, generally up to 400 mg and preferably up to 200 mg, of a compound of formula (I). The average range of the compound of formula (I) in the dosage unit is within the range from 0.2 to 20 mg per kg of body weight. The dosage unit may be administered one time or several times per day, depending on the amount of compound (I) and of the kind for preparation. Thus, if the preparation has a release effect, the administration may be at least one time per day. On the other hand, if the dosage unit contains a relatively small amount of compound (I) within the mentioned range, a repeated administration per day will be advisable while for dosage units with a relatively large amount only one administration per day may be sufficient. The duration of treatment may be e.g. from 1 to several weeks or up to some years. The preferred injectable solutions and dosage unit forms are those containing 1-(5-hydroxyhexyl)-3,7-dimethylxanthine or 7-(5-hydroxyhexyl)-1,3-dimethylxanthine.

The compound contained in the pharmaceutical compositions according to the invention are novel with the exception of 1-(5-hydroxyhexyl)-3,7-dimethylxanthine and 7-(3-hydroxypentyl)-1,3-dimethylxanthine. The first-mentioned xanthine derivative may be prepared according to "Archiv der Pharmazie", Vol. 299 (1966), page 455, the last mentioned xanthine derivative may be prepared according to "Dissertationes Pharmaceuticae et Pharmacologicae" Vol. XX, pages 497 to 505, 1968.

According to a further feature of the invention there is provided a compound of the formula (I) wherein $R_1$ is a member selected from the group consisting of ω-hydroxyalkyl having from 5 to 8 carbon atoms and in which the hydroxyl is separated from the xanthine nucleus by at least two carbon atoms, unbranched (ω-1)-hydroxyalkyl having 5, 7 or 8 carbon atoms, branched (ω-1)-hydroxyalkyl having from 5 to 8 carbon atoms and in which the hydroxyl is separated from the xanthine nucleus by at least two carbon atoms, methyl and —H;

$R_2$ is a member selected from the group consisting of ω-hydroxyalkyl having from 5 8 carbon atoms and in which the hydroxyl is separated from the xanthine nucleus by at least two carbon atoms, unbranched (ω-1)-hydroxyalkyl having from 5 to 8 carbon atoms, branched (ω-1)-hydroxyalkyl having from 5 to 8 carbon atoms and in which hydroxyl is separated from the xanthine nucleus by at least two carbon atoms, and methyl; and $R_3$ is a member selected from the group consisting of ω-hydroxyhexyl unbranched (ω-1)-hydroxyalkyl having from 5 to 8 carbon atoms, branched (ω-1)-hydroxyalkyl having from 5 to 8 carbon atoms and in which the hydroxyl is separated from the xanthine nucleus by at least two carbon atoms, methyl and —H;

one and only one of $R_1$, $R_2$ and $R_3$ being ω- or (ω-1)-hydroxyalkyl. Those compounds are preferred (wherein one of the groups $R_1$, $R_2$ and $R_3$ is an ω- or (ω-1)-hydroxyalkyl group having from 5 to 8 carbon atoms and being branched or unbranched, but in which the carbon atom to which the hydroxy group is bound is separated from the xanthine nucleus by at least 2, preferably at least 3 carbon atoms, that or those of $R_1$ and $R_3$ which are other than a hydroxyalkyl group, being hydrogen or methyl and the same or different, and $R_2$ is said hydroxyalkyl group or methyl.

One embodiment of the invention provides a compound of formula (I) wherein one of $R_1$, $R_2$ and $R_3$ is an unbranched or branched (ω-1)-hydroxyalkyl.

According to a further feature of the invention there is provided a compound of formula (I), wherein either $R_1$ is an unbranched (ω-1)-hydroxyalkyl group having 5, 7 or 8 carbon atoms and each of $R_2$ and $R_3$ is methyl, or wherein each of $R_1$ and $R_3$ is methyl and $R_2$ is an unbranched (ω-1)-hydroxyalkyl group having from 5 to 8 carbon atoms, or wherein each of $R_1$ and $R_2$ is methyl and $R_3$ is an unbranched (ω-1)-hydroxyalkyl group having 5 to 8carbon atoms.

According to a still further feature of the invention there is provided a compound of formula (I), wherein one of the groups $R_1$, $R_2$ and $R_3$ is a branched (ω-1)-hydroxyalkyl group having from 5 to 8 carbon atoms, in which the hydroxy group is separated from the xanthine nucleus by at least two, preferably at least 3 carbon atoms, the radicals $R_1$ and $R_3$ which are other than a hydroxyalkyl group are hydrogen or methyl and the same or different, and $R_2$ in said hydroxyalkyl or methyl.

The following are specific examples of the new compounds acccording to the invention: 1-(4-hydroxypentyl)-3,7-dimethylxanthine (melting point 100° C.), 1-(6-hydroxyheptyl)-3,7-dimethylxanthine, 1-(7-hydroxyoctyl)-3,7-dimethylxanthine, 7-(4-hydroxypentyl)-1,3-dimethylxanthine (melting point 84° C.), 7-(5-hydroxyhexyl)-1,3-dimethylxanthine (melting point 93°–94° C.), 7-(6-hydroxyheptyl)-1,3-dimethylxanthine (melting point 109° C.), 7-(7-hydroxyoctyl)-1,3-dimethylxanthine, 3-methyl-7-(5-hydroxyhexyl)-xanthine, 1,3-dimethyl-7-(6-hydroxyhexyl)-xanthine, 1-(6-hydroxyhexyl)-3,7-dimethylxanthine, 1-(6-hydroxyhexyl)-3-methylxanthine, 3-methyl-7-(6-hydroxyhexyl)-xanthine and the corresponding hydroxyheptyl and hydroxpentyl compounds, for example 1-(2-methyl-3-hydroxybutyl)-3,7-dimethylxanthine (syrupy), 1,3-dimethyl-7-(2-methyl-3-hydroxybutyl)-xanthine (syrupy), 1,3-dimethyl-7-(7'hydroxyheptyl)-xanthine and 3-methyl-7-(7'-hydroxyheptyl)-xanthine.

The compounds of formula (I) as defined in claim 1 and used in the compositions according to the invention may be prepared by a process wherein (a) an alkali metal salt of a compound of formula (I), but which contains—instead of the hydroxyalkyl group and if desired additionally instead of a methyl group—as a radical $R_1$, $R_2$ or $R_3$ a hydrogen atom, is reacted in conventional manner with one mol of a hydroxy alkyl halide or (b) an alkali metal salt of a compound of the formula (I) as defined in claim 1, but in which at least one of the radicals $R_1$ and $R_3$ is a hydrogen atom and one of the radicals $R_1$, $R_2$ and $R_3$ is a hydroxyalkyl radical, is reacted in solution with an alkylating agent or (c) a compound of formula (I) as defined in claim 1, but in which one of the radicals $R_1$, $R_2$ and $R_3$ is a halogenalkyl radical instead of the hydroxyalkyl radical, is reacted with an alkali metal salt of a lower fatty acid having 1 to 6 carbon atoms to obtain the corresponding carboxylic acid ester, which is hydrolytically split to obtain the products of the invention or (d) wherein a compound of formula (I) having an oxygen atom in the place of the hydroxy group is reduced whereby the carbonyl group is transformed to a hydroxyl group or (e) wherein water is added to a compound of formula (I) having an ($\omega$-1) alkenyl group in the place of the hydroxyalkyl group.

The $\omega$-hydroxyalkyl compounds are prepared, e.g. according to embodiment (a), for example, by reacting an alkali metal salt of a compound of formula (I) (wherein one of $R_1$, $R_2$ and $R_3$ represents a hydrogen atom and the other two, which may be the same or different, are methyl or hydrogen atoms) with an $\omega$-hydroxyalkyl halide containing 5 to 8 carbon atoms. The alkali metal salt may be prepared by addition of an alkali, in the presence of a solvent, for example in an alcohol with 1 to 3 carbon atoms, e.g. methanol, ethanol or isopropanol, or in an aprotic solvent such as formamide, dimethylformamide or dimethyl sulphoxide. The alkali may in particular be the form of aqueous sodium hydroxide solution, solid sodium hydroxide or a sodium alcoholate or a corresponding potassium compound. The reaction is preferably carried out by adding the $\omega$-hydroxyalkyl halide to the alkali metal salt and heating the solution.

A method of preparation according to embodiment (b) comprises reacting an alkali metal salt of a hydroxyalkyl-xanthine having hydrogen atoms in the 1- and/or 7-positions with suitable alkylating agents, for example methyl halides, e.g. methyl chloride, bromide and iodine, or dimethylsulphate, preferably in aqueous-organic solution. The aqueous-organic solution consists of a mixture of water with organic solvents being miscible with water, e.g. the above-mentioned alcohols and aprotic solvents.

A method preparation of the new compounds according to embodiment (c) comprises reacting a compound of formula (I), wherein one of the groups $R_1$, $R_2$ and $R_3$ represents a haloalkyl group containing from 5 to 8 carbon atoms and the other two, which may be the same or different, are methyl, with an alkali metal salt of a carboxylic acid containing 1 to 6 carbon atoms, whereby a carboxylic acid ester is produced, and subsequently hydrolysing this ester. The hydrolysis is preferably effected in the presence of an acid, for example dilute sulphuric acid, advantageously at temperatures from 10° to 100° C. This process gives almost quantitative yields of the hydroxyalkyl-xanthine compounds according to the invention.

The reduction according to embodiment (d) is applied with particular advantage to compounds which have the oxo atom in ($\omega$-1)-position, and may be effected by means of conventional reducing agents which bring about the conversion of an oxo group into a hydroxyl group. The reduction can for example take place with complex borohydrides, aluminium alkoxide, magnesium or sodium in an alcohol with 1 to 3 C-atoms, particularly ethanol, methanol or isopropanol, with sodium amalgam, with zinc in aqueous potassium hydroxide solution, with lithium aluminum hydride or by means of catalytic hydrogention e.g. with palladium on charcoal, Raney nickel or copper chromium oxide catalysts or metallic platinum prepared from platinum oxide and finely dispersed in the solution. Particularly advantageous is the reduction of the ketoalkyl theophyllines and theobromines with sodium borohydride in an aqueous and/or alcoholic solution.

The reaction according to embodiment (e) is advantageously carried out in an aqueous solution or suspension and advisably in the presence of an acid, such as a mineral acid, e.g. sulphuric acid, a hydrogen halide, nitric acid, phosphoric acid, a sulphonic acid such as trifluoromethyl sulphonic acid or an ion exchanger having —$HO_3S$— groups. If desired this reaction may be carried out in the presence of an organic solvent, such as 1,4-dioxane, benzene or toluene, which is inert to dilute acids. This embodiment is in general carried out at a temperature in the range from 40° to 150° C., preferably from 60° to 120° C. The termination of the reaction may be determined by chromatographic methods. The desired final products may be obtained from the aqueous phase by extraction with suitable agents, e.g. chlorinated hydrocarbons such as methylene chloride or chloroform. Where in addition to the aqueous phase an organic phase is present, further portions of the desired products may be obtained by distilling off the solvent, if desired under reduced pressure.

A further subject of the invention consists of compounds of formula (I) having an ($\omega$-1)-alkenyl group in place of the hydroxyalkyl group, and pharmaceutical compositions containing them. Thus, in these compounds one of the groups $R_1$, $R_2$ and $R_3$ is an ($\omega$-1)-alkenyl group—preferably an unbranched group—having from 4 to 8 carbon atoms, preferably from 5 to 8 carbon atoms, in which the double bond is separated from the xanthine nucleus by at least one carbon atom and in which those radicals $R_1$ and $R_3$ are other than alkenyl group, are hydrogen or methyl and the same or different, and $R_2$ is said alkenyl group or methyl. These compounds may be used as starting materials in the reaction of embodiment (e). Suitable compounds are e.g. 1-(3-butenyl)-3,7-dimethylxanthine, 1-(2-methyl-3-butenyl)-3,7-dimethylxanthine, 1-(4-pentenyl)-3,7-dimethylxanthine, 1-(5-hexenyl)-3,7-dimethylxanthine, 1,3-dimethyl-7-(3-butenyl)-xanthine, 1,3-dimethyl-7-(2-methyl-3-butenyl)-xanthine, 1,3-dimethyl-7-(4-pentenyl)-xanthine, 1,3-dimethyl-7-(5-hexenyl)-xanthine, 1,3-dimethyl-7-(6-heptenyl)-xanthine.

The compounds of the inventions have various pharmaceutical effects. Thus, they increase the cerebral or muscular blood circulation. They also have a broncholytic or fibrinolytic effect or they show an inhibition motility.

According to a still further feature of the invention there is provided a method of improving the cerebral blood flow of a person which comprises administering to a person afflicted with insufficiency of cerebral blood circulation a cerebral blood circulation-improving effective amount of a compound of formula (I), wherein one of the groups $R_1$ and $R_3$ is an unbranched hydroxyalkyl group having from 5 to 8 carbon atoms and the other one is methyl or an effective amount of any other compound covered by formula (I) as defined above.

According to a yet still further feature of the invention there is provided a pharmaceutical product for the treatment of diseases involving insufficiency of cerebral blood flow which comprises (a) a pharmaceutical composition according to the invention and (b) written or printed directions to use the pharmaceutical composition in the treatment of diseases involving insufficiency of cerebral blood flow. The pharmaceutical composition is conveniently provided in a suitable container such as a bottle, an ampoule or a vial. If desired, the container may itself bear printed or written directions for the intended use of the product. Alternatively, or additionally, the container may be accompanied by separate written or printed directions for such use, e.g. a leaflet describing the intended medical use of the product concerned. Such leaflets are frequently referred to as "package inserts" or "stuffer leaflets". The directions will preferably state the pharmacological actions and indications of the compounds as well as providing information such as dosage to be administered and possible side effects.

The invention is illustrated by the following examples and the comparisons with 7-(2-hydroxyethyl)-1,3-dimethylxanthine, 7-(2,3-dihydroxypropyl)-1,3-dimethylxanthine and 1-(2-hydroxypropyl)-3,7-dimethylxanthine relative to the action on cerebral blood flow in cats.

EXAMPLES

1. Preparation of the medicament

Injection solution 100 g of 1-(5-hydroxyhexyl)-3,7-dimethylxanthine and 35 g of sodium chloride are made up to 700 ml with distilled water. The solution is filtered sterile and introduced into 7 ml ampoules. Alternatively the solution may be sterilised after filling.

For the preparation of 1000 coated tablets 100 g of 1-(5-hydroxyhexyl)-3,7-dimethylxanthine, 20 g of lactose, 30 g of maize starch, 8.5 g of talc, 0.5 g of colloidal silicic acid and 1 g of magnesium stearate are mixed and pressed into coated tablet cores weighing 160 mg. For the tablet coating mixture 44.57 g of cane sugar, 23.4 g of talc, 8 g of cellulose acetate phthalate, 2.24 g of castor oil and very small additions of wax, titanium dioxide and gum arabic are used in such a way that the final weight of the coated tablets is 240 mg.

Investigation of cerebral blood flow of cats

Method

The test principle of K. Golenhofen, H. Hensel and G. Hildebrandt (Perfusion measurements with heat conducting elements in research and clinic, Thieme Verlag Stuttgart 1963) is used. The test animals are cats under chloralose urethane narcosis (70+200 mg/kg i.p.). The top of the skull is opened in the area of the frontal gyrus marginalis or suprasylvicus. The measurements are performed with a modified surface measuring head according to Hensel (cf. Pflügers Arch. vol. 268, (1959), page 604), applied after opening the dura of the cerebral cortex. The action time is given as the half value time and the intensity of action is determined according to Golenhofen et al. as a heat transfer factor $\lambda$. The recording was performed with thermoprobes using a two-channel Pluvograph of Hartmann & Braun, Frankfurt am Main, Germany. Other circulation parameters recorded at the same time were fed to a Hellige multi-channel recorder.

TABLE 1

Action of various hydroxyalkylxanthines and 1,3-dimethyl-xanthine-ethylene-diamine on the cerebral blood flow of cats using a thermoprobe according to Hensel.

| Substance | Dosis in mg/kg i.v. | Change of blood perfusion $\Delta \lambda$ | half-value time in min. | n | Toxicity in mg/kg (mouse) |
|---|---|---|---|---|---|
| 1,3-dimethyl-7-(5-hydroxy-hexyl)-xanthine | 5 | +0.18 | 1.8 | 4 | 250–500 i.p. |
| 1,3-dimethyl-7-(6-hydroxy-heptyl)-xanthine | 1 | +0.70 | 0.6 | 2 | 250–500 i.p. |
|  | 2 | +0.42 | 1.2 | 6 |  |
|  | 5 | +1.17 | 1.8 | 6 |  |
| 1-(5-hydroxy-hexyl)-3,7-dimethyl-xanthine | 3 | +1.80 | 4.3 | 2 | 195 i.v. |
|  | 5 | +1.55 | 5.0 | 2 |  |
|  | 10 | +2.65 | 3.5 | 2 |  |
| 7-(2-hydroxy-ethyl)-1,3-dimethyl-xanthine (comparison) | 5 | −0.50 | 0.23 |  |  |
|  | 10 | −1.33 | 0.50 |  |  |
|  | 25 | −2.17 | 6.73 |  |  |
|  | 50 | −5.33 | 7.17 |  |  |
|  | 100 | −6.00 | 8.00 |  |  |
| 1-(2-hydroxy-propyl)-3,7-dimethyl-xanthine (comparison) | 5 | −0.25 | 0.50 |  |  |
|  | 10 | −0.50 | 1.50 |  |  |
|  | 25 | ±0 | — |  |  |
|  | 50 | −5.25 | 17.5 |  |  |
|  | 100 | −10.00 | 6.5 |  |  |
| 7-(2,3-di-hydroxy-propyl)-1,3-di-methylxanthine | 5 | ±0 | — |  |  |
|  | 10 | −0.12 | 1.7 |  |  |
|  | 25 | −0.23 | 6.0 |  |  |
|  | 50 | +0.20 | 3.0 |  |  |
|  | 100 | −0.05 | 3.0 |  |  |
| theophylline-ethylenediamine (comparison) | 1 | +0.19 | 1.8 | 7 | 217 i.p. |
|  | 2 | +0.15 | 1.8 | 2 |  |
|  | 5 | +0.18 | 3.3 | 8 |  |
|  | 10 | +0.53 | 1.7 | 7 |  |

As it is evident from the table the xanthine compounds of the invention have an effect which is at least equal, but predominantly essentially stronger with respect to the blood perfusion increase combined with an essentially lower toxicity than the comparison substances.

EXAMPLE 2

A pharmaceutical granulate containing, in addition to adjuvants e.g. starch and talc, 10 g of 1-(5-hydroxyhexyl)-3,7-dimethylxanthine, 2 g of vitamin $B_2$ and 1.5 g of vitamin $B_1$ hydrochloride is suitable for the elimination of perfusion disturbances e.g. for increasing the coronary blood flow as well as for use in geriatrics.

EXAMPLE 3

Preparation of 7-(5-hydroxyhexyl-1,3-dimethylxanthine 15 g of 7-(5-oxohexyl)-1,3-dimethylxanthine are dissolved in 100 ml of ethanol and mixed portionwise at room temperature with 3.8 g of sodium borohydrate (110% of theory) in solid form or in alcoholic suspension. At the end of addition stirring takes place for 30 minutes. Subsequently heating takes place to boiling temperature. At this time the reaction is completed. The course of the reaction is followed by thin layer chromatography. The solvent is evaporated on a rotary evaporator. The residue is boiled e.g. with 50 ml isopropanol or ethyl acetate. The insoluble substance is filtered off and discarded. The extract is crystallised by evaporation. 7-(5-hydroxyhexyl)-1,3-dimethylxanthine of m.p. 93° to 94° C. in a yield of 86% by weight is obtained. The substance after chromatography with silica gel $F_{254}$ (Merck sheets) as the absorbent and with a mixture of benzene and acetone in a volume ratio of 60:40 as the eluting agent has a $R_f$-value of 0.15.

EXAMPLE 4

In analogy to example 3, the following 1-[(ω-1)-hydroxy]-alkyl-3,7-dimethylxanthines and 7-[(ω-1)-hydroxy]alkyl-1, 3-dimethylxanthines of chain length $C_5$ to $C_8$ are obtained from the corresponding oxoalkyl compounds, which products after chromatography on the indicated system had the following $R_f$-values

|  | $R_f$-value |
| --- | --- |
| 1-(4-hydroxypentyl)-3,7-dimethylxanthine | 0.15 |
| 1-(6-hydroxyheptyl)-3,7-dimethylxanthine | 0.23 |
| 1-(7-hydroxyoctyl)-3,7-dimethylxanthine | 0.27 |
| 7-(4-hydroxypentyl)-1,3-dimethylxanthine | 0.13 |
| 7-(6-hydroxyheptyl)-1,3-dimethylxanthine | 0.12 |
| 7-(7-hydroxyoctyl)-1,3-dimethylxanthine | 0.23 |

The structures of the compounds are in accordance with the UV—, IR—, nuclear and mass spectra.

EXAMPLE 5

(A) 1,3-dimethylxanthine is dissolved in a mixture of 250 ml of water and 750 ml of n-propanol by adding an equimolar quantity of sodium hydroxide and heating. An equivalent amount of 1,6-dibromohexane is quickly added to the solution and the mixture is boiled under reflux for 1 hour. After evaporation of the n-propanol, 7-(6-bromohexyl)-1,3-dimethylxanthine is isolated.

(B) 3.4 g of 1,3-dimethyl-7-(6-bromohexyl)-xanthine are boiled overnight under reflux in 50 ml of glacial acetic acid to which 1 ml of acetic anhydride and 5 g of potassium acetate have been added. After evaporated of the solvent by distillation in vacuo the residue is dissolved in 50 ml of 5% sulfuric acid on the addition of 20 ml methanol. The solution is boiled under reflux for 1 hour. The mixture is extracted with chloroform. The chloroform phase is washed until it is neutral and concentrated in vacuo. 1,3-dimethyl-7-(6-hydroxyhexyl)-xanthine having a melting point of 80° C. is obtained in a yield of more than 90%.

(C) Alternative preparation of 1,3-dimethyl-7-(6-hydroxyhexyl)-xanthine 1,3-dimethyl-7-(6-bromohexyl)-xanthine is refluxed overnight with a sixfold molar excess of potassium acetate with the addition of catalytic quantities, such as 2 mol percent, referred to the xanthine, of potassium iodide in a mixture of 5 ml of acetic anhydride and 200 ml of glacial acetic acid. The solvent is evaporated in vacuo. The residue is dissolved in water and the pH of the solution is adjusted to a value of 7 with 4N sodium hydroxide. The solution is then extracted with chloroform. The isolated 1,3-dimethyl-7-(acetoxyhexyl)-xanthine is subsequently hydrolysed to the corresponding hydroxyalkyl compound by boiling with 5% sulfuric acid.

EXAMPLE 6

1-(6-bromohexyl)-3,7-dimethylxanthine is obtained from 3,7-dimethylxanthine analogously to Example 5A). From this product 1-(6-hydroxyhexyl)-3,7-dimethylxanthine having a melting point of 98° to 100° C. is obtained in a yield of more than 90% by analogous methods to those described in Examples 5B and 5C.

EXAMPLE 7

9.2 g of 3-methyl-xanthine are dissolved in a mixture of 10 ml of water and 200 ml of methanol by adding 2.2 g of solid sodium hydroxide and heating. 10 g of 6-bromohexanol-(1) are then added.

After boiling overnight, the alcohol is distilled off and the solution is extracted with methylene chloride at a pH-value of 10. The extract is removed. At a pH-value of 7.2 the mixture is again extracted with methylene chloride and the solvent is distilled off. The residue is recrystallised from a small quantity of isopropanol. 3-methyl-7-(6-hydroxyhexyl)-xanthine having a melting point of 219° to 220° C. is obtained in a yield of about 90%.

EXAMPLE 8

13.2 g of 1-(2-methyl-3-oxobutyl)-3,7-dimethylxanthine are dissolved in 100 ml of ethanol and 4.2 g of sodium borohydride are added in portions at ambient temperature. The mixture is then stirred for 30 minutes and is subsequently heated to its boiling point. The solution is concentrated to a quarter of its volume and filtered. After a further concentration 1-(2-methyl-3-hydroxybutyl)-3,7-dimethylxanthine is obtained as an oil. The reaction proceeds quantitatively. Thin layer chromatography on silica gel plates, eluent benzene/acetone (60:40 by volume) indicates a product with an $R_f$-value of 0.28, compared with 0.50 for the starting material, IR, NMR and mass spectrography studies confirm the structure.

EXAMPLE 9

1.32 g of 1,3-dimethyl-7-(2-methyl-3-oxobutyl)-xanthine are reacted with 0.42 g of sodium borohydride analogously to Example 8. The product is not crystalline. If analogous to that of Example 8 a similar chromatogram is prepared, the 1,3-dimethyl-7-(2-methyl-3-hydroxybutyl)-xanthine has an $R_f$-value of 0.21, compared with 0.35 for the starting compound. IR, NMR and mass spectrography studies confirm its structure.

EXAMPLE 10

(A) 10.3 g of 1-bromohexene-(5) are reacted at 120° C. with 20.2 g of sodium theobromine in 200 ml of dimethylformamide, while stirring, until the termination of the reaction is determined from a thin layer chromatogram, i.e. after about 6 to 8 hours. The solvent is then distilled off under reduced pressure. The residue is dissolved at 20° C. in 100 ml of methylene chloride, separated from the undissolved sodium bromide and purified in a column of neutral aluminia in order to remove small amounts of dark contaminations. 1-(5-hexenyl)-3,7-dimethylxanthine crystallizes from n-hexane in colourless needles melting at 76° C. The yield is 24.1 g (92 percent of the theory). After thin layer chromatography with silica gel 60 $F_{254}$ (Merck DC-sheets) as the absorbent and with a mixture of benzene and acetone in the volume ratio of 60:40 as the eluting agent the substance has a $R_f$-value of 0.47. With a mixture of nitromethane, benzene and pyridine in a volume ratio of 20:10:3 as the eluting agent the substance has a $R_f$-value of 0.60. In both cases it is indicated by UV-light. However when using the latter eluent the pyridine content thereof has to be removed in view of its property to extinguish fluorescence by heating to 50° C. under reduced pressure.

(B) For the preparation of 1-(5-hydroxyhexyl)-3,7-dimethylxanthine 2.6 g of 1-(5-hexenyl)-3,7-dimethylxanthine are boiled with 25 ml of 1-normal sulfuric acid for 24 hours. A small portion of the clear solution is tested for the degree of addition of water. The desired final product does extinguish fluorescence at a $R_f$-value from 0.30 to 0.37 while using the nitromethane-benzene-pyridine-eluent. After termination of the reaction the product is neutralized and extracted with methylene chloride from which 1-(5-hydroxyhexyl)-3,7-dimethylxanthine is obtained in colourless crystals having after recrystallization from methanol a melting point of 126° C. The yield is 2.6 g (93 percent of theory).

EXAMPLES 11 TO 16

In a manner analogous to that described in Example 10 the following compounds have been prepared:

| | Melting point |
|---|---|
| (11) 1-(4-hydroxypentyl)-3,7-dimethylxanthine | 100° C. |
| (12) 1-(2-methyl-3-hydroxybutyl)-3,7-dimethylxanthine | syrupy |
| (13) 1,3-dimethyl-7-(2-methyl-3-hydroxybutyl)-xanthine | syrupy |
| (14) 1,3-dimethyl-7-(4-hydroxypentyl)-xanthine | 84° C. |
| (15) 1,3-dimethyl-7-(5-hydroxyhexyl)-xanthine | 93–94° C. |
| (16) 1,3-dimethyl-7-(6-hydroxyheptyl)-xanthine | 109° C. |

EXAMPLE 17

18 g of theophylline are added under stirring at room temperature to a solution of 4.1 g of sodium hydroxide in 50 ml of water and 50 ml of methanol. After stirring the mixture at 70° C. 15.8 g of 7-chloro-1-heptanol are added. The mixture is then maintained at 70° C. for 22 hours and then it is subjected to evaporation under reduced pressure until it is dry. The residue is dissolved in 150 ml of 1-N-sodium hydroxide and the mixture is extracted with methylene chloride. After washing out with water and drying over sodium sulfate the methylene chloride solution is concentrated under reduced pressure and the oily residue is several times recrystallized from diisopropyl ether. 6.3 g of 1,3-dimethyl-7-(7'-hydroxyheptyl)-xanthine are obtained (yield, referred to reacted theophylline, =79.3%).

EXAMPLE 18

16.6 g of 3-methylxanthine are added at 25° C. to a solution of 4.1 g of sodium hydroxide in 50 ml of methanol and 50 ml of water. After heating the mixture for one hour at 70° C. 15.8 g of 7-chloro-1-heptanol are added to the clear solution. After maintaining the mixture for further 24 hours at 70° C. it is cooled to 20° C.; the precipitate is separated and is again precipitated from an alkaline solution (pH=13.5) by slowly, dropwise adding a 33% sulfuric acid until a pH-value of 10 is obtained. After repeated recrystallization from water 10.3 g of 3-methyl-7-(7'-hydroxyheptyl)-xanthine, melting point 239° to 240° C., are obtained in a yield of 63.6%, referred to the reacted 3-methyl-xanthine.

EXAMPLES 19 TO 23

The following compounds have been prepared analogously to Example 10 (A).

| | melting point °C. |
|---|---|
| (19) 1-(3-butenyl)-3,7-dimethyl-xanthine | 115 |
| (20) 1-(4-pentenyl)-3,7-dimethyl-xanthine | 94 |
| (21) 1,3-dimethyl-7-(3-butenyl)-xanthine | 110 |
| (22) 1,3-dimethyl-7-(4-pentenyl)-xanthine | 92 |
| (23) 1,3-dimethyl-7-(5-hexenyl)-xanthine | 42 |

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What is claimed is:

1. A pharmaceutical composition containing as one of plural components and as sole essential active ingredient, a cerebral-blood-flow-increasing amount of a compound of the formula

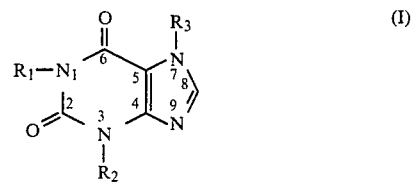

wherein
$R_1$ is a member selected from the group consisting of ω-hydroxyalkyl having from 5 to 8 carbon atoms and in which the hydroxyl is separated from the xanthine nucleus by at least two carbon atoms, unbranched (ω-1)-hydroxyalkyl having 5 to 8 carbon atoms, branched (ω-1)-hydroxyalkyl having from 5 to 8 carbon atoms and in which the hydroxyl is separated from the xanthine nucleus by at least two carbon atoms, methyl and —H;

$R_2$ is a member selected from the group consisting of ω-hydroxyalkyl having from 5 to 8 carbon atoms and in which the hydroxyl is separated from the xanthine nucleus by at least two carbon atoms, unbranched (ω-1)-hydroxyalkyl having from 5 to 8 carbon atoms, branched (ω-1)-hydroxyalkyl having from 5 to 8 carbon atoms and in which the hydroxyl is separated from the xanthine nucleus by at least two carbon atoms, and methyl; and $R_3$ is a member selected from the group consisting of unbranched ω or (ω-1)-hydroxyalkyl having from 5 to 8 carbon atoms, branched (ω-1)-hydroxyalkyl having from 5 to 8 carbon atoms and in which the hydroxyl is separated from the xanthine nucleus by at least two carbon atoms, methyl and —H;

one and only one of $R_1$, $R_2$ and $R_3$ being ω- or (ω-1)-hydroxyalkyl.

2. A pharmaceutical composition as claimed in claim 1 wherein one of the groups $R_1$, $R_2$ and $R_3$ is a hydroxyalkyl group having from 5 to 8 carbon atoms in which the carbon atom to which the hydroxy group is bound is separated from the xanthine nucleus by at least 2 carbon atoms, and each other of said groups is methyl.

3. A pharmaceutical composition as claimed in claim 1 wherein either $R_1$ or $R_3$ is a hydroxyalkyl group having from 5 to 8 carbon atoms and wherein $R_2$ and the other one of $R_1$ and $R_3$ is methyl.

4. A pharmaceutical composition as claimed in claim 1 wherein the hydroxyl of the hydroxyalkyl group is in the ω- or (ω-1)-position.

5. A pharmaceutical composition as claimed in claim 1 wherein the hydroxyl group of the hydroxyalkyl is in the (ω-1)-position and the hydroxyalkyl group is unbranched.

6. A pharmaceutical composition as claimed in claim 1 wherein the compound is 1-(5-hydroxyhexyl)-3,7-dimethylxanthine.

7. A pharmaceutical composition as claimed in claim 1 in dosage unit form containing up to 1000 mg of the compound.

8. A composition according to claim 1 containing (a) carrier, diluent or excipient and (b) the essential ingredient in an essentially non-toxic concentration which is effective for increasing cerebral blood flow of a subject to which the composition is administered.

9. A pharmaceutically-acceptable composition according to claim 1 containing
(a) a pharmaceutically-acceptable diluent for active ingredient in the composition and
(b) a sufficient concentration of active ingredient to counteract insufficiency of cerebral blood circulation in a host to which the composition is administered; the essential active ingredient of the composition being a compound of the formula

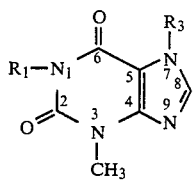

wherein one of $R_1$ and $R_3$ is unbranched (ω-1)-monohydroxyalkyl having from 5 to 8 carbon atoms and the other is methyl.

10. A pharmaceutically-acceptable composition as claimed in claim 9 wherein the compound is 1-(5-hydroxyhexyl)-3,7-dimethylxanthin.

11. A pharmaceutically-acceptable composition according to claim 9 in the form of an injectable solution of the essential active ingredient in sterile water.

12. A sterile aqueous pharmaceutically-acceptable composition according to claim 9 in dosage unit form containing
(a) a pharmaceutically-acceptable diluent for active ingredient in the composition and
(b) from 10 to 1000 milligrams of the essential active ingredient.

13. A solid pharmaceutically-acceptable composition according to claim 9 in dosage unit form containing
(a) a pharmaceutically-acceptable diluent for active ingredient in the composition and
(b) from 10 to 1000 milligrams of the essential active ingredient.

14. A sterile aqueous composition according to claim 9.

15. A solid composition according to claim 9.

16. A sterile aqueous composition according to claim 10.

17. A solid composition according to claim 10.

18. A composition according to claim 1 wherein $R_3$ is ω-hydroxyhexyl.

19. A pharmaceutical composition as claimed in claim 8 wherein one of the groups $R_1$, $R_2$ and $R_3$ is a hydroxyalkyl group having from 5 to 8 carbon atoms in which the carbon atom to which the hydroxy group is bound is separated from the xanthine nucleus by at least 2 carbon atoms and each other of said groups is methyl.

20. A non-toxic pharmaceutical composition comprising active component in addition to carrier, diluent or excipient and characterized by the active component which consists essentially of a cerebral-blood-flow-increasing amount of a compound of the formula

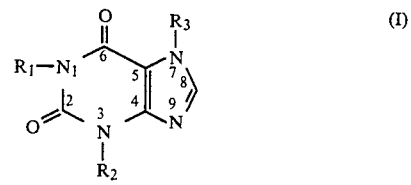

wherein
$R_1$ is a member selected from the group consisting of ω-hydroxyalkyl having from 5 to 8 carbon atoms and in which the hydroxyl is separated from the xanthine nucleus by at least two carbon atoms, unbranched (ω-1)-hydroxyalkyl having 5, 7 or 8 carbon atoms, branched (ω-1)-hydroxyalkyl having from 5 to 8 carbon atoms and in which the hydroxyl is separated from the xanthine nucleus by at least two carbon atoms, methyl and —H;

$R_2$ is a member selected from the group consisting of ω-hydroxyalkyl having from 5 to 8 carbon atoms and in which the hydroxyl is separated from the xanthine nucleus by at least two carbon atoms unbranched (107 -1)-hydoxyalkyl having from 5 to 8 carbon atoms, branched (ω-1)-hydroxyalkyl having from 5 to 8 carbon atoms and in which the hydroxyl is separated from the xanthine nucleus by at least two carbon atoms, and methyl; and $R_3$ is a member selected from the group consisting of ω-hydroxyhexyl, unbranched (ω-1)-hydroxyalkyl having from 5 to 8 carbon atoms, branched (ω-1)-hydroxyalkyl having from 5 to 8 carbon atoms and in which the hydroxy is separated from the xanthine nucleus by at least two carbon atoms, methyl and —H;

one and only one of $R_1$, $R_2$ and $R_3$ being ω- or (ω-1)-hydroxyalkyl.

* * * * *

UNITED STATES PATENT AND TRADEMARK OFFICE
CERTIFICATE OF CORRECTION

PATENT NO. : 4,576,947

DATED : March 18, 1986

INVENTOR(S) : Heinz-Joachim Hinze et al.

It is certified that error appears in the above-identified patent and that said Letters Patent is hereby corrected as shown below:

The term of this patent subsequent to May 7, 2002 has been disclaimed.

Signed and Sealed this

Eighth Day of July 1986

[SEAL]

Attest:

DONALD J. QUIGG

Attesting Officer

Commissioner of Patents and Trademarks